(12) United States Patent
Warren et al.

(10) Patent No.: US 6,545,185 B1
(45) Date of Patent: Apr. 8, 2003

(54) PREPARATION OF KETONES FROM ALDEHYDES

(75) Inventors: Jack S. Warren, Blountville, TN (US); David R. Westphal, Chanhassen, MN (US); Steve J. Zoubek, Otsego, MN (US)

(73) Assignee: EagleView Technologies, Inc., Minneapolis, MN (US)

( * ) Notice: Subject to any disclaimer, the term of this patent is extended or adjusted under 35 U.S.C. 154(b) by 0 days.

(21) Appl. No.: 09/978,778

(22) Filed: Oct. 17, 2001

Related U.S. Application Data

(60) Provisional application No. 60/279,851, filed on Mar. 29, 2001.

(51) Int. Cl.[7] ............................................. C07C 45/72
(52) U.S. Cl. ....................... 568/338; 568/343; 568/346; 568/354
(58) Field of Search ................................. 568/343, 338, 568/346, 354

(56) References Cited

U.S. PATENT DOCUMENTS

| | | | |
|---|---|---|---|
| 3,410,909 A | 11/1968 | Fleischer et al. | |
| 3,453,331 A | 7/1969 | Hargis et al. | |
| 3,466,334 A | 9/1969 | Young et al. | |
| 3,660,491 A | 5/1972 | Thigpen et al. | |
| 3,966,822 A | 6/1976 | Fukui et al. | |
| 4,060,555 A | 11/1977 | Peterson et al. | |
| 4,505,738 A | 3/1985 | Gsell | |
| 4,515,626 A | 5/1985 | Szczepanski | |
| 4,528,400 A | 7/1985 | Cryberg et al. | |
| 4,570,021 A | 2/1986 | Cryberg et al. | |
| 4,590,292 A | 5/1986 | Blackwell et al. | |
| 4,693,745 A | 9/1987 | Brunner | |
| 4,797,152 A | 1/1989 | Brunner | |
| 4,803,268 A | 2/1989 | Brunner et al. | |
| 4,872,902 A | 10/1989 | Brunner | |
| 4,874,899 A | 10/1989 | Hoelderich et al. | |
| 4,883,878 A | 11/1989 | Amato et al. | |
| 4,964,846 A | 10/1990 | Gais et al. | |
| 5,026,916 A | 6/1991 | Tobler | |
| 5,124,293 A | 6/1992 | Lindfors et al. | |
| 5,366,957 A | 11/1994 | Cain et al. | |
| 5,434,152 A | 7/1995 | Huffman et al. | |
| 5,453,545 A | 9/1995 | Burello et al. | |
| 5,565,399 A | 10/1996 | Fraenkel et al. | |
| 5,629,455 A | 5/1997 | Kaufhold et al. | |
| 5,656,573 A | 8/1997 | Roberts et al. | |
| 5,849,928 A | 12/1998 | Hawkins | |
| 5,877,330 A | 3/1999 | Kishimoto et al. | |
| 6,087,538 A | 7/2000 | Teles et al. | |

FOREIGN PATENT DOCUMENTS

| | | |
|---|---|---|
| DE | 36 37 788 A1 | 5/1988 |
| DE | 3637788 * | 5/1988 |
| DE | 197 26 666 A1 | 12/1998 |
| EP | 0 085 996 B1 | 8/1983 |
| EP | 0 085 996 A2 | 8/1983 |
| EP | 0 418 175 B1 | 3/1991 |
| EP | 0 507 013 B1 | 10/1992 |
| EP | 0 527 036 B1 | 2/1993 |
| EP | 0 527 037 B1 | 2/1993 |
| EP | 0 560 482 B1 | 9/1993 |
| EP | 0 609 798 A1 | 8/1994 |
| EP | 0 682 659 B1 | 11/1995 |
| GB | 1 435 639 | 5/1976 |
| WO | WO 99/02476 | 1/1999 |
| WO | WO 99/24409 | 5/1999 |
| WO | WO 00/30448 | 6/2000 |

OTHER PUBLICATIONS

Cannon et al., "Acylation Studies. I Methyl Cyclopropyl Ketone," *Journal of Organic Chemistry*, 17(5):685–692 (May 1952).

Claridge et al., "Conversion of Propanal to Pentan–3–one Using Lanthanide Oxides", *J. Chem. Soc. Faraday Trans.*, 89(7):1089–1094 (1993).

International Search Report for PCT/US99/25372 (2 pages).
International Search Report for PCT/US00/24458 (6 pages).
Kamimura et al., "Vapor–Phase Synthesis of Symmetric Ketone from Alcohol over $CeO_2$–$Fe_2O_3$ Catalysts", The Chemical Society of Japan, *Chemistry Letter 2000*, pp. 232–233.

Novartis, Palisade™ EC Directions for use and conditions of sale and warranty (5 pages).

Rhone–Poulenc, Balance (TM) WDG Herbicide, Material Safety Data Sheet prepared Sep. 3, 1998 (7 pages).

* cited by examiner

*Primary Examiner*—Johann Richter
*Assistant Examiner*—Sikarl A. Witherspoon
(74) *Attorney, Agent, or Firm*—Popovich & Wiles, P.A.

(57) ABSTRACT

A method and apparatus for the production of ketones via a one-step synthesis from aldehydes. In the method of the invention, an aldehyde, a carboxylic acid, and a source of oxygen, such as water, are allowed to react in the vapor phase in a catalytic tube reactor. Asymmetrical ketones, such as methyl cyclopropyl ketone, are particularly desirable reaction products.

22 Claims, 1 Drawing Sheet

PREPARATION OF KETONES FROM ALDEHYDES

This application claims the benefit of provisional application Serial No. 60/279,851, filed Mar. 29, 2001, the contents of which are hereby incorporated herein by reference.

FIELD OF THE INVENTION

The present invention relates generally to the preparation of ketones. More particularly, this invention relates to a method and apparatus for preparing ketones via catalytic reaction from an aldehyde and a carboxylic acid.

BACKGROUND OF THE INVENTION

In general, unsymmetrical ketones are useful as intermediates for the production of numerous specialty chemicals. More specifically, methyl cyclopropyl ketone (MCPK) has a variety of current and potential uses including, among others, the production of specialty agricultural and pharmaceutical compounds.

Numerous literature references cite and disclose various well-known processes for the preparation of ketones. These processes include oxidation of secondary alcohols, Friedel-Crafts acylation, reaction of acid chlorides with organo cadmium compounds, acetoacetic ester synthesis and decarboxylation from acids, among others.

Text and literature references also detail problems associated with using these processes to produce ketones. These include problems such as the unavailability and/or cost of raw materials, the requirement of multi-stage processing, the low conversion of the raw materials and/or the low selectivity of the desired ketones, and the production of corrosive or hard to separate products.

Ketone production processes have also been described in the patent literature. For example, U.S. Pat. Nos. 4,528,400 and 4,570,021 disclose a process for the preparation of unsymmetrical ketones by a catalytic vapor phase reaction using reactants such as ketones with carboxylic acids. However, laboratory trials using acetone and cyclopropanecarboxylic acid resulted in the production of high quantities of gamma-butyrolactone, several pentenones and pentanones, but no MCPK.

U.S. Pat. Nos. 3,410,909 and 3,453,331 disclose processes for the preparation of symmetrical and unsymmetrical ketones from aldehydes containing up to 8 carbons in a non-cyclic saturated aliphatic chain.

German Patent Disclosure No. P36 37 788.0 (1986) discloses a specific condensation reactor process for the preparation of methyl cyclopropyl ketone (MCPK) from cyclopropanecarboxylic acid or its derivatives. However, although examples from this patent show raw material conversion of from 58 to 99 percent and selectivity to MCPK of 42 to 75 percent, the liquid hourly space velocity (LHSV) or weight hourly space velocity (WHSV) values of less than 1 (i.e., 0.25 to 0.99) minimize the industrial usefulness of this condensation reactor process.

European Patent Application No. 0 085 996 also discloses processes for the preparation of unsymmetric aliphatic ketones at atmospheric pressures (or slightly above) and at relatively low WHSV.

U.S. Pat. No. 3,966,822 (Fukui et al.) discloses the preparation of ketones from aldehydes in the presence of zirconium oxide and various other catalysts. U.S. Pat. No. 3,466,334 (Young et al.) discloses synthesis of ketones from an aldehyde and an acid in the presence of a catalyst comprised of an alumina-supported oxidized form of lithium. U.S. Pat. No. 3,453,331 (Hargis et al.) discloses a process for the synthesis of ketones from aldehydes using various alumina-supported oxidized forms of various metals. WO 00/30448, published Jun. 2, 2000 and entitled "Method and Apparatus for the Preparation of Ketones", describes methods for the catalyst-mediated production of ketones. In general, an acid or aldehyde or derivatives thereof and a carboxylic acid are reacted in the presence of a catalyst to produce a desired ketone.

The most common industrial processes for the production of ketones typically involve the reaction of an acid in the presence of a catalyst. Catalyzed reactions such as these can be low in yield due to side reactions and/or the reactant throughput can be low due to system requirements.

Thus, there is a need in the art for a method to produce ketones in high yields in a cost-effective manner.

SUMMARY OF THE INVENTION

The present invention relates to a method and an apparatus for producing ketones via a one step synthesis from aldehydes. This synthesis has good selectivity and conversion rates. Particularly desirable reaction products include asymmetrical ketones such as methyl cyclopropyl ketone (MCPK). The method and apparatus of the present invention utilizes readily available and relatively inexpensive raw materials and results in high conversion and selectivity rates.

Generally, the raw materials used in this invention include an aldehyde, a carboxylic acid, and a source of oxygen, such as water.

In a preferred embodiment, this invention involves the reaction of cyclopropanecarboxaldehyde, acetic acid, and water at elevated temperatures in the presence of a catalyst to form methyl cyclopropyl ketone (MCPK). Vaporized reactants flow through a tube reactor provided with a suitable catalyst.

In one aspect, this invention is a method for the production of a ketone comprising providing a tube reactor having a catalytic bed; providing a carboxylic acid, a source of oxygen; and an aldehyde, and passing the carboxylic acid, the source of oxygen, and the aldehyde, each in a vapor phase, through the catalytic bed at a weight hourly space velocity greater than 1 to form the ketone. The ketone may be an asymmetrical ketone and the carboxylic acid and the aldehyde may be heated before entering the tube reactor. Preferably, the weight hourly space velocity is in the range of 1 to 20. In a preferred embodiment, the weight hourly space velocity is in the range of 2 to 20. In another preferred embodiment, the weight hourly space velocity is in the range of 5 to 20. The reacting may take place in two or more tube reactors connected in parallel. Preferably, the catalyst is a theoretical monolayer on a solid support. The method may also include the step of recovering the ketone. In preferred embodiments, the source of oxygen is water. In another preferred embodiment, the ketone is methyl cyclopropyl ketone, the aldehyde is cyclopropanecarboxaldehyde, and the acid is acetic acid. The weight ratio of the carboxylic acid: source of oxygen: aldehyde may range from 1:1:1 to 20:1:1. The catalyst may be selected from MgO, $TiO_2$, $ZrO_2$, ZnO, $CeO_2$, and $Ce_2O_3$. A preferred catalyst is $CeO_2$ on a $TiO_2$ support wherein there is about 15 to 20% $CeO_2$ per gram of $TiO_2$. The method may be a continuous process.

In a second aspect, this invention is a method of preparing a ketone comprising providing a plurality of tube reactors, each having a catalytic bed; providing a raw material feed comprised of a carboxylic acid, a source of oxygen, and an aldehyde, to produce the ketone; selectively passing the raw material feed through the catalytic bed of at least one of the plurality of tube reactors at a temperature of between about 350° C. and 500° C. and a weight hourly space velocity of greater than 1; and recovering the ketone. This method may also include selectively stopping the passage of raw material feed through the catalytic bed of the at least one tube reactor and passing the raw material feed through the catalytic bed of at least one of the plurality of tube reactors, and/or regenerating the catalytic bed of the at least one tube reactor through which the passage of raw material feed has been stopped. Preferably, the catalytic bed includes a $CeO_2/TiO_2$ catalyst structure having about 15 to 20% $CeO_2$ per gram of $TiO_2$.

In a third aspect, this invention is a process for the production of a ketone comprising reacting acetic acid with cyclopropanecarboxaldehyde and with water to form methyl cyclopropyl ketone; wherein the reacting occurs in the vapor phase and in the presence of a catalyst.

In a fourth aspect, this invention is a process for the preparation of a compound of formula (I)

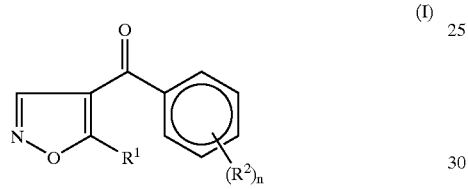

(I)

wherein:
$R^1$ is cycloalkyl having from three to six ring carbon atoms which is unsubstituted or which has one or more substituents selected from the group consisting of $R^4$ and halogen; $R^2$ is halogen; straight- or branched-chain alkyl having up to six carbon atoms which is substituted by one or more —$OR^5$; cycloalkyl having from three to six carbon atoms; or a member selected from the group consisting of nitro, cyano, —$CO_2R^5$, —$NR^5R^6$, —$S(O)_pR^7$, —$O(CH_2)_mOR^5$, —$COR^5$, —$N(R^8)$ $SO_2R^7$, —$OR^7$, —OH, —$OSO_2R^7$, —$(CR^9R^{10})_rSO_qR^{7a}$, —$CONR^5R^6$, —$N(R^8)$—$C(Z)Y$, —$(CR^9R^{10})NR^8R^{11}$ and $R^4$; n is zero or an integer from one to three; when n is greater than one, then the groups $R^2$ are the same or different; m is one, two or three; p is zero, one or two; q is zero, one or two; t is an integer from one to four; $R^3$ is straight- or branched-chain alkyl group containing up to six carbon atoms which is unsubstituted or which has one or more substituents selected from the group consisting of halogen, —OR, —$CO_2R^5$, —$S(O)_pR^7$, phenyl or cyano; or phenyl which is unsubstituted or which has one or more substituents selected from the group consisting of halogen, —$OR^5$ and $R^4$; $R^4$ is straight- or branched-chain alkyl, alkenyl or alkynyl having up to six carbon atoms which is unsubstituted or is substituted by one or more halogen; $R^5$ and $R^6$, which are the same or different, are each hydrogen or $R^4$; $R^7$ and $R^{7a}$ independently are $R^4$, cycloalkyl having from three to six ring carbon atoms, or —$(CH_2)_w$-phenyl wherein phenyl is unsubstituted or is substituted by from one to five $R^{12}$ which are the same or different; w is zero or one; $R^8$ is hydrogen; straight- or branched-chain alkyl, alkenyl or alkynyl having up to ten carbon atoms which is unsubstituted or is substituted by one or more halogen; cycloalkyl having from three to six ring carbon atoms; —$(CH_2)_w$-phenyl wherein phenyl is unsubstituted or is substituted by from one to five $R^{12}$ which are the same or different; or —$OR^{13}$; $R^9$ and $R^{10}$ independently are hydrogen or straight- or branched-chain alkyl having up to six carbon atoms which is unsubstituted or is substituted by one or more halogen; $R^{11}$ is —$S(O)_qR^7$ or —$C(Z)Y$; $R^{12}$ is halogen; straight- or branched-chain alkyl having up to three carbon atoms which is unsubstituted or is substituted by one or more halogen; or a member selected from the group consisting of nitro, cyano, —$S(O)_pR^3$ and —$OR^5$; Y is oxygen or sulfur; Z is $R^4$, —$NR^8R^{13}$, —$NR^8NR^{13}R^{14}$,—$SR^7$ or —$OR^7$; and $R^{13}$ and $R^{14}$ independently are $R^8$, or an agriculturally acceptable salt or metal complex thereof, which process comprises:
(i) reacting a compound of formula (II)

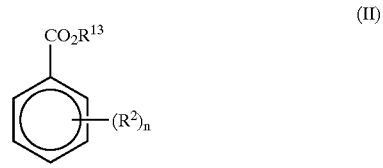

(II)

wherein $R^{15}$ is a straight- or branched-chain alkyl group having up to six carbon atoms with a compound of formula (III)

(III)

in an aprotic solvent in the absence of a base to form a compound of formula (IV)

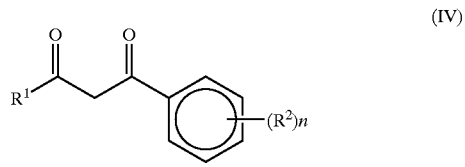

(IV)

(ii) reacting a compound of formula (IV) with a compound that contains a leaving group L [such as alkoxy or N,N-dialkylamino, esp. ethoxy and $CH(OCH_2CH_3)_3$] to form a compound of formula (V)

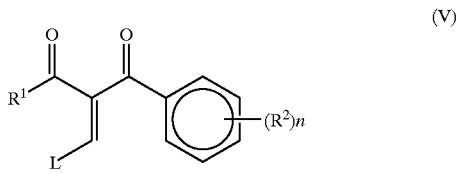

(V)

(iii) reacting a compound of formula (V) with hydroxylamine or a salt of hydroxylamine to form a compound of formula (I), wherein the process further comprises producing the compound of formula (III) by providing a catalytic bed; providing a raw material feed comprising a carboxylic acid, water, and $R^1COH$ in the ratio of from 1:1:1 to 20:1:1; passing the raw material feed through the catalytic bed at a temperature of between about 350° C. and 500° C. at a weight hourly space velocity greater than one; and separating the compound of formula (III).

Preferably, the carboxylic acid is acetic acid. In a fifth aspect, this invention is the method for the preparation of a compound of formula (X)

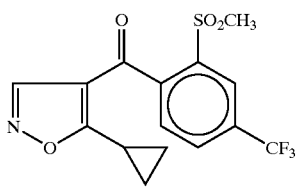

(X)

comprising:

(i) reacting a compound of formula (XI)

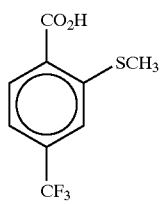

(XI)

with a compound of formula (XII)

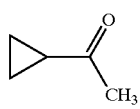

(XII)

to form a compound of formula (XIII)

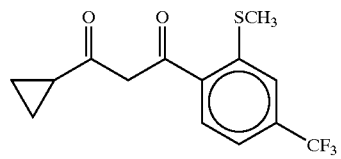

(XIII)

(ii) reacting a compound of formula (XIII) with CH(OCH$_2$CH$_3$)$_3$ to form a compound of formula (XIV)

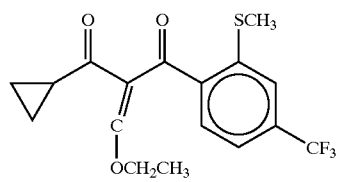

(XIV)

(iii) reacting a compound of formula (XIV) with hydroxylamine or a salt of hydroxylamine to form a compound of the formula (XV)

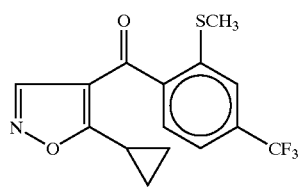

(XV)

(iv) reacting a compound of formula (XV) with chloroperbenzoic acid to form a compound of the formula (X), wherein the process further comprises producing the compound of formula (XII) by providing a catalytic bed; providing a raw material feed comprised of a carboxylic acid, water, and R$^1$COH in the ratio of from 1:1:1 to 20:1:1; passing the raw material feed through the catalytic bed at a temperature of between about 350° C. and 500° C. at a weight hourly space velocity greater than one; and separating the compound of formula (XII).

DETAILED DESCRIPTION OF THE PREFERRED EMBODIMENTS

Figure 1:
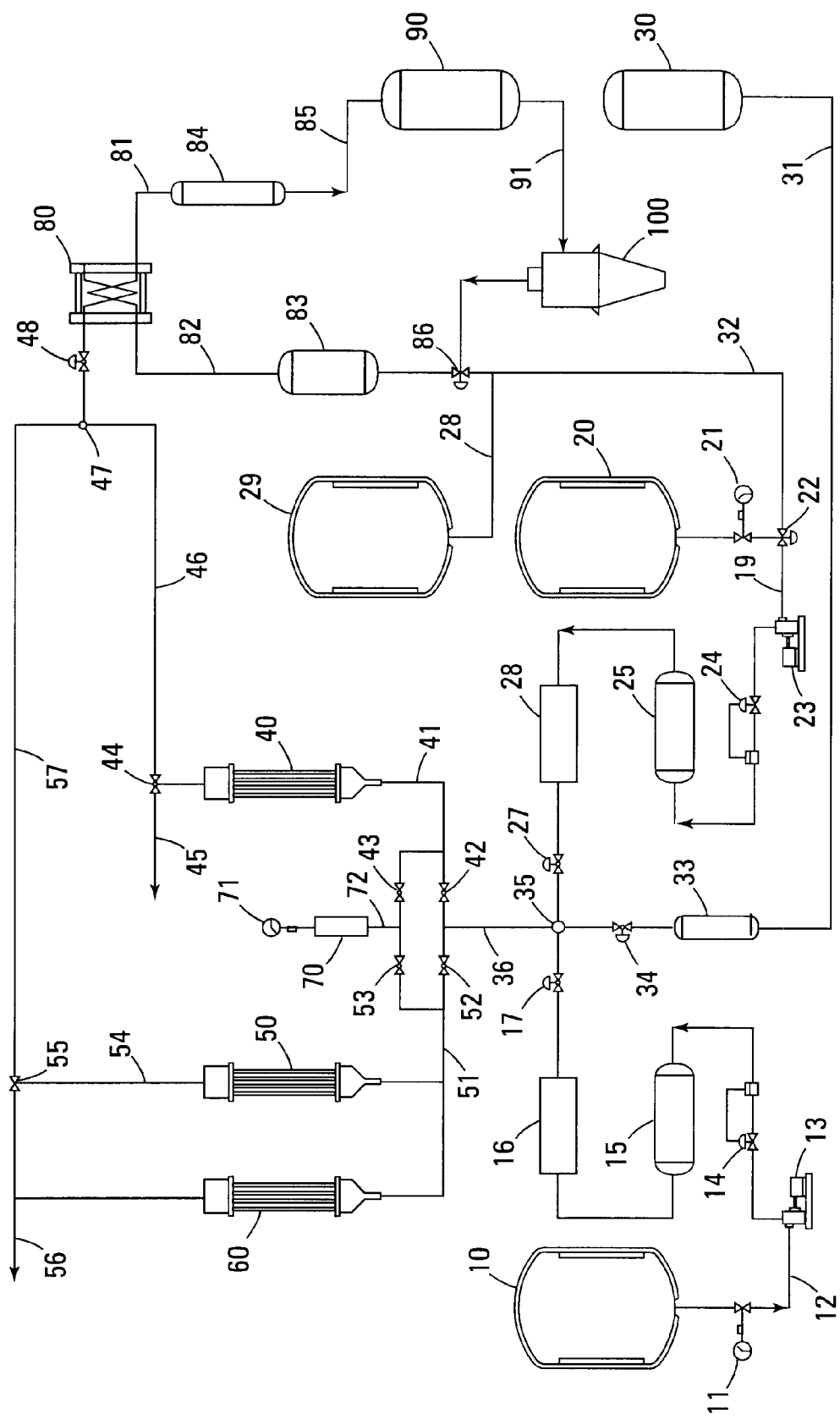
FIG. 1 is a schematic illustration of the method and apparatus of the present invention.

The apparatus and method of this invention are applicable to a wide variety of ketones and more specifically asymmetrical ketones having the following formula:

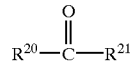

The ketones are derived from the catalyzed reaction in the vapor phase of an aldehyde R$^{20}$ COH with an acid R$^{21}$COOH in the presence of a source of oxygen. The acid includes precursors and derivatives of the acid, such as the anhydride. R$^{20}$ is selected from modified or substituted straight chain or cyclic (C$_1$–C$_{12}$)-alkyls, phenyl and substituted phenyls, and R$^{21}$ is selected from modified or substituted straight chain or cyclic (C$_1$–C$_{12}$)-alkyls, phenyl and substituted phenyls.

In a preferred embodiment, R$^{20}$ is cyclopropyl (C$_3$H$_5$) and R$^{21}$ is methyl (CH$_3$); i.e., the catalyzed reaction of cyclopropane carboxaldehyde and acetic acid or its precursors or derivatives in the presence of a source of oxygen produces methyl cyclopropyl ketone (MCPK).

The source of oxygen preferably is water, however, other sources of oxygen, such as oxygen gas (O$_2$), hydrogen peroxide (H$_2$O$_2$), ozone (O$_3$), oxygen enriched inert gas or oxygen enriched water vapor and other oxygen sources that are known to one of skill in the art may be used.

In addition to a method for making methyl cyclopropyl ketone (MCPK), the process of this invention may be used to make other desired ketones, as shown by the following formulas:

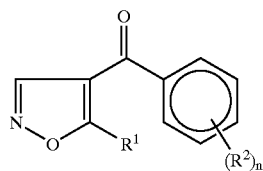

(I)

wherein:

$R^1$ is cycloalkyl having from three to six ring carbon atoms which is unsubstituted or which has one or more substituents selected from the group consisting of $R^4$ and halogen; $R^2$ is halogen; straight- or branched-chain alkyl having up to six carbon atoms which is substituted by one or more —$OR^5$; cycloalkyl having from three to six carbon atoms; or a member selected from the group consisting of nitro, cyano, —$CO_2R^5$, —$NR^5R^6$, —$S(O)_pR^7$, —$O(CH_2)_mOR^5$, —$COR^5$, —$N(R^8)SO_2R^7$, —$OR^7$, —OH, —$OSO_2R^7$, —$(CR^9R^{10})_tSO_qR^{7a}$, —$CONR^5R^6$, —$N(R^8)$—$C(Z)Y$, —$(CR^9R^{10})NR^8R^{11}$ and $R^4$;

n is zero or an integer from one to three; when n is greater than one, then the groups $R^2$ are the same or different; m is one, two or three; p is zero, one or two; q is zero, one or two; t is an integer from one to four;

$R^3$ is straight- or branched-chain alkyl group containing up to six carbon atoms which is unsubstituted or which has one or more substituents selected from the group consisting of halogen, —$OR^5$, —$CO_2R^5$, —$S(O)_pR^7$, phenyl or cyano; or phenyl which is unsubstituted or which has one or more substituents selected from the group consisting of halogen, —$OR^5$ and $R^4$; $R^4$ is straight—or branched-chain alkyl, alkenyl or alkynyl having up to six carbon atoms which is unsubstituted or is substituted by one or more halogen; $R^5$ and $R^6$, which are the same or different, are each hydrogen or $R^4$; $R^7$ and $R^{7a}$ independently are $R^4$, cycloalkyl having from three to six ring carbon atoms, or —$(CH_2)_w$-phenyl wherein phenyl is unsubstituted or is substituted by from one to five $R^{12}$ which are the same or different; w is zero or one; $R^8$ is hydrogen; straight- or branched-chain alkyl, alkenyl or alkynyl having up to ten carbon atoms which is unsubstituted or is substituted by one or more halogen; cycloalkyl having from three to six ring carbon atoms; —$(CH_2)_w$-phenyl wherein phenyl is unsubstituted or is substituted by from one to five $R^{12}$ which are the same or different; or —$OR^{13}$; $R^9$ and $R^{10}$ independently are hydrogen or straight- or branched-chain alkyl having up to six carbon atoms which is unsubstituted or is substituted by one or more halogen;

$R^{11}$ is —$S(O)_qR^7$ or —$C(Z)Y$;

$R^{12}$ is halogen; straight- or branched-chain alkyl having up to three carbon atoms which is unsubstituted or is substituted by one or more halogen; or a member selected from the group consisting of nitro, cyano, —$S(O)_pR^3$ and —$OR^5$;

Y is oxygen or sulphur;

Z is $R^4$, —$NR^8R^{13}$, —$NR^8NR^{13}R^{14}$, —$SR^7$ or —$OR^7$; and $R^{13}$ and $R^{14}$ independently are $R^8$, or an agriculturally acceptable salt or metal complex thereof.

The compounds having formula (I) are produced by a process comprising:

(i) reacting a compound of formula (II)

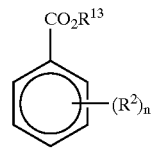

(II)

wherein $R^{15}$ is a straight- or branched-chain alkyl group having up to six carbon atoms with a compound of formula (III):

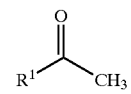

(III)

in an aprotic solvent in the absence of a base to form a compound of formula (IV):

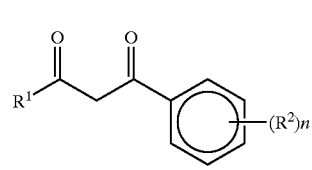

(IV)

(ii) reacting a compound of formula (IV) with a compound that contains a leaving group L [such as alkoxy or N,N-dialkylamino, particularly ethoxy and $CH(OCH_2CH_3)_3$] to form a compound of formula (V)

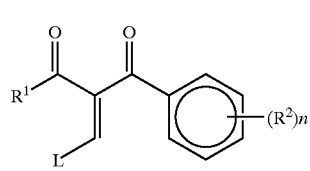

(V)

(iii) reacting a compound of formula (V) with hydroxylamine or a salt of hydroxylamine to form a compound of formula (I), wherein the process further comprises producing the compound of formula (III) by:

providing a catalytic bed;

providing a raw material feed comprised of a carboxylic acid, water, and $R^1COH$ and in the ratio of from 1:1:1 to 20:1: 1;

passing the raw material feed through the catalytic bed at a temperature of between about 350° C. and 500° C. at a weight hourly space velocity greater than one; and separating the compound of formula (III).

Preferably, the carboxylic acid is acetic acid.

The process of this invention also applies to compounds having formula (X):

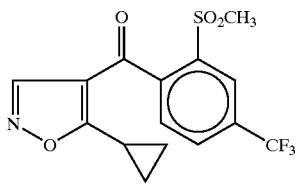
(X)

comprising:
(iii) reacting a compound of formula (XI)

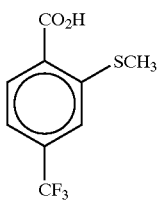
(XI)

with a compound of formula (XII)

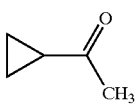
(XII)

to form a compound of formula (XIII)

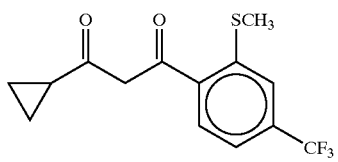
(XIII)

(iv) reacting a compound of formula (XIII) with CH(OCH$_2$CH$_3$)$_3$ to form a compound of formula (XIV)

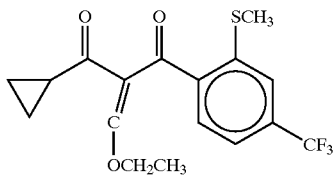
(XIV)

(iii) reacting a compound of formula (XIV) with hydroxylamine or a salt of hydroxylamine to form a compound of the formula (XV)

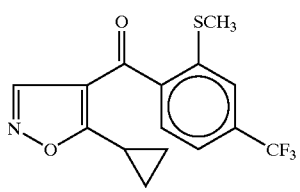
(XV)

(iv) reacting a compound of formula (XV) with chloroperbenzoic acid to form a compound of the formula (X)

wherein the process further comprises producing the compound of formula (XII) by providing a catalytic bed; providing a raw material feed comprised of acetic acid, water, and cyclopropyl aldehyde in the ratio of from 1:1:1 to 20:1:1; passing the raw material feed through the catalytic bed at a temperature of between about 350° C. and 500° C. at a weight hourly space velocity greater than one; and separating the compound of formula (XII).

In a most preferred embodiment, the catalytic reaction in the vapor phase of acetic acid, cyclopropanecarboxaldehyde, and water results in the production of methyl cyclopropyl ketone.

The catalyst preferably is selected from Al$_2$O$_3$, MgO, TiO$_2$, ZrO$_2$, ZnO, CeO$_2$, and Ce$_2$O$_3$, as well as mixtures and various combinations of these oxides. In a preferred embodiment, the catalyst is CeO$_2$. In a most preferred embodiment, the catalyst is a monolayer of CeO$_2$ on TiO$_2$.

In another preferred embodiment, the weight ratio of carboxylic acid, water, and aldehyde ranges from 1:1:1 to 20:1:1, and in a most preferred embodiment this weight ratio is 4:1:1. The reaction preferably takes place in one or more tube reactors. Multiple reactors may be connected in parallel so that one reactor can be regenerated while the other is in use.

In the preferred embodiment described immediately below, the aldehyde, the acid, and the water are held in separate feed tanks. The liquid reactants flow through lines into heaters and preferably are separately preheated to the gaseous phase. They are then combined in the gaseous phase and introduced into a tube reactor containing catalyst. Alternatively, the reactants may be introduced into the tube reactor as liquids and heated to vaporize there.

The reactants are fed into the catalytic reactor at elevated temperatures (ranging from about 350 to 500° C.) and elevated pressure; (ranging from 50 to 500 psi (344.7 to 3447 MPa)). The tube reactor is held at a temperature ranging from 350 to 500° C. The gas phase reactants mix together in weight ratio of about ranging from 1:1:1 to 20:1:1 (i.e., the ratio of acid to water to aldehyde) and flow into the reactor. The optimum ratio is determined empirically and will vary depending upon the particular aldehyde, carboxylic acid and oxygen source.

The reactants exit their tanks as liquids and are fed through lines equipped with feed pumps into heaters and thence into the catalytic tube reactor. Any heater effective at heating vapor phase components to temperatures up to about 450° C. is useful in the practice of this invention, but preferably the heater is an electric heater such as a superheater or vaporizer, available from AccuTherm, Inc. of Monroe City, Mo.

The heated reactants flow into the tube reactor where they are exposed to the catalyst and react to produce the desired products. Preferably, reactants are fed into the bottom of the reactor so that the reactant materials flow upwardly through the reactor. To minimize undesired co-products as well as "coking" of the catalyst and thus "plugging" of the reactor, the optimum reaction temperature of the reactant feed stream is determined. It is also desirable to heat the catalyst bed to such optimum temperature prior to the introduction of the reactant materials.

The raw materials are fed through a reactor at a rate sufficient to provide a liquid or weight hourly space velocity of greater than 1, preferably in the range of 1 to 20. As used herein and as known by those of skill in the art, weight (or liquid) hourly space velocity (WHSV or LHSV) is the amount of raw material (unit weight or volume) per unit weight or volume of catalyst per hour.

Tube reactors useful in the practice of this invention are preferably conventional stainless steel catalytic tube reactors that are filled with various combinations of inert filler material and a catalyst. Inert filler material may comprise glass beads between about 3 to 10 millimeters (mm) in diameter, or may include one or more of stainless steel beads, lava rock and sand. The filler material prevents laminar flow and promotes both turbulent flow and uniform exposure to the catalyst. Preferred catalysts and supports are described further below.

In addition, the apparatus is equipped with a means to regenerate the catalyst in the tube reactor. When regeneration is desired, air/$O_2$/$N_2$ or other gases known to those skilled in the art are caused to flow through the reactor heated to 400° C. to 550° C. Typically catalyst regeneration is carried out in about 8 to 12 hours.

Further, it may be desirable to regenerate the catalyst bed in a tube reactor without interruption of a production run. In this case, at least two tube reactors are connected in parallel, so that the reactants can flow through one tube reactor while another reactor undergoes regeneration. For example, three tube reactors are illustrated in FIG. 1.

Turning now to FIG. 1, a preferred embodiment of the method and apparatus of this invention is illustrated. The system and the method will be described with respect to MCPK. Unless otherwise indicated, all percentages are by weight.

Feed tank 10 contains acetic acid in a liquid state. The acetic acid flows from tank 10 via conduit 12 which is fitted with nitrogen purge valve 11. When it is desired to purge the line of acid, valve 11 is opened and nitrogen gas is allowed to flow through. The acetic acid feeds into feed pump 13 and through flow control device 14 which meters the reactant into heaters 15 and 16. The acetic acid is heated to about 250° C. in heater 15 and to about 450° C. in heater 16. The acid remains within the heaters for a time sufficient for the acid to reach the desired temperature. Valve 17 is positioned in conduit 12 to control the flow of acetic acid on its way to mixing/proportioning valve 35.

Feed tank 30 contains water that flows via conduit 31 to heater/vaporizer 33 where the water is converted to steam. Control valve 34 is used to control the flow of steam to mixing/proportioning valve 35.

Feed tank 20 contains cyclopropanecarboxaldehyde in a liquid state. The aldehyde flows from tank 20 via conduit 19 which is fitted with nitrogen purge valve 21 and valve 22. When it is desired to purge the line of aldehyde, valves 21 and 22 are opened to the source of nitrogen (thus closing the flow of aldehyde) and nitrogen gas allowed to flow through. The aldehyde feeds into feed pump 23 and through flow control device 24 which meters it into heaters 25 and 26. The aldehyde is heated to about 250° C. in heater 25 and to about 450° C. in heater 26. The aldehyde remains within the heaters for a time sufficient for aldehyde to reach the desired temperature. Valve 27 is positioned in conduit 19 to control the flow of aldehyde on its way to mixing/proportioning valve 35. Mixing/proportioning valve 35 permits the control of reactant ratio.

The reactants flow through mixing/proportioning valve 35, into conduit 36 and into one or more tube reactors. Three tube reactors 40, 50, and 60 are shown, and it is to be understood that there is no limit on the number of tube reactors that could be set up in parallel in the apparatus. One or more of the reactors can be used during a single production run depending upon which valves are open to permit flow to a reactor. Valves 42 and 52, for example, could both be opened for reactant flow to reactors 40 and 50, via conduits 41 and 51 respectively. Similar valves (not shown) would control the flow to tube reactor 60.

The reactants enter the tube reactors in a vapor phase. The pressure of the reactant stream as it enters the tube reactor is greater than ambient, and typically ranges from about 50 to about 500 psi (344.7 to 3447 MPa). The tube reactors are loaded with cerium oxide ($CeO_2$) catalyst on a titania ($TiO_2$) support. A preferred surface area for the support is 150 to 220 $m^2$/g and the catalyst is present at a loading of 15 to 20 weight percent. The weight hour space velocity (WHSV) ranges from 1 to 20.

When it is desired to regenerate catalyst in tube reactor 40, for example, valve 42 is closed to stop the flow of reactant to tube reactor 40. The reaction then could continue in another tube reactor (e.g., 50 and/or 60) during regeneration. Reservoir 71 contains regeneration gases such as air/$O_2$/$N_2$. The regeneration gas flows through heater 70 and is heated to between 400° C. and 550° C. It flows through conduit 72 into conduit 41 when valve 43 is opened. The air/$O_2$/$N_2$ regeneration cycle may require 8 to 12 hours to complete, and depends upon the volume of catalyst bed and degree of coking or contamination of the catalyst.

The reaction products (i.e., desired ketone, any unreacted material, and/or any undesired reaction byproducts) flow out of tube reactors 40 and 50 via conduits 46 and 54, respectively, fitted with flow valves 44 and 55. These lines may further be equipped with vents 45 and 56 for the venting of regeneration or purge gases. FIG. 1 illustrates that the reaction product from tube reactor 50 flows via conduit 57 through flow valves 47 and 48 into heat exchanger 80. The reaction products flow from tube reactor 40 through conduit 46 to valves 47 and 48 which lead into heat exchanger 80. The heat exchanger condenses the reaction product and permits separation of unreacted aldehyde, which flows via conduit 82 into collection reservoir 83. Unreacted aldehyde can then flow into line 32 for use in the reaction when valve 86 is open.

Optional tank 29 also can be provided. Tank 29 is used if needed to contain recovered aldehyde, which flows into it via conduit 28. Flow into and out of tank 29 would be controlled by one or more valves, not shown.

Desired product is separated via heat exchanger 80 and flows via conduit 81 into condenser 84. Conduit 85 carries the product from condenser 84 to intermediate reservoir 90 from which it is fed via conduit 91 into distillation unit 100, which separates the desired product from by products and unreacted acid.

It is believed that the use of a source of oxygen in this reaction results in the regeneration of the catalyst during the reaction, and thus more efficient use of the catalyst. This results in a selective catalytic process for the aldehyde/acid condensation reaction to the ketone. The reaction is believed to proceed by conversion of the cyclopropanecarboxaldehyde to its acid, and then the reaction of the acid with the acetic acid to produce the ketone.

An experiment was done using a quartz microreactor. This permitted the use of pulsed reagents and quantification of the products. All pulses were 100 microliters in 0.5 mL groups. Product was detected by mass spectroscopy. The Table shows that when a source of oxygen is present, the reaction produces a good yield of MCPK. HAc is acetic acid; CCAld is cyclopropanecarboxaldehyde; and CCA is cyclopropylcarboxylic acid.

| Feed composition (molar ratios) | Temperature (° C.) | % Conversion to CCA | Wt % Selectivity to MCPK |
|---|---|---|---|
| 4/1 HAc/CCAld | 390 | 32 | 9 |
| 4/1 HAc/CCAld | 440 | 9.8 | 0 |
| 4/1 HAc/CCAld | 390 | 38 | 8 |
| 4/1 HAc/CCAld | 440 | 49 | 7 |
| 4/1 HAc/CCAld | 390 | 66 | 11 |
| 4/1 HAc/CCAld | 440 | 24 | 14 |
| 4/1/1 HAc/H20/CCAld | 390 | 10.2 | 37 |
| 4/1/1 HAc/H20/CCAld | 440 | 11.2 | 68 |

Catalysts

In the most preferred embodiment of this invention, the catalyst is $CeO_2$ on $TiO_2$. This catalyst is prepared by the incipient wetness method, as further described below. The weight percent of catalyst ranges from 10 to 20%.

The chemical composition, porosity, density, effective surface area, shape, size and cross section of catalyst support materials are selected by the user depending upon the needs of the reaction and the equipment. Examples of suitable catalyst supports include metals or metal oxides such as alumina, magnesia, silica, titania, zirconia, zinc oxide and mixtures thereof and naturally occurring clay material such as montmorillonite or kaolin. These existing catalyst support materials generally have effective surface areas ranging from about 20 to 500 $m^2$ per gram. Preferred substrates for use in the present invention include substrates such as aluminum oxide ($Al_2O_3$), zinc oxide (ZnO), zirconium oxide ($ZrO_2$), titanium oxide ($TiO_2$), or combinations of these oxides.

To prepare the catalyst structure in accordance with the present invention, a catalyst useful in the production of ketones is applied to the surface area of the catalyst support by methods known in the art. For example, cerium oxide ($CeO_2$) catalyst is prepared by impregnating a porous titanium oxide ($TiO_2$) cylindrical structure with a solution of a predetermined concentration of cerium acetate hydrate ($Ce(O_2 CCH_3)_3 \cdot 1.5H_2O$) using the incipient wetness method (drop-wise), at ambient temperature. Following such impregnation, the catalyst support is dried at 450° C. for 12 hours.

The hydrate solution is prepared by dissolving 200 grams per liter of aqueous solution. This produces 1.0 gram of $CeO_2$/2.0 grams of cerium acetate hydrate. Any desirable percentage can be obtained by using 10 milliliters of this solution for each one gram of catalyst needed. For example, for approximately 5 wt % $CeO_2$ catalyst, 50 milliliters of the solution is used per 100 grams of catalyst support. For impregnation of catalyst on the catalyst support greater than 5%, multiple applications are used, with an intermediate drying step of 120° C., to insure uniform coverage. For approximately 10 wt % $CeO_2$ catalyst, two 50 milliliter solutions are used. The resulting catalyst support with impregnated catalyst is then dried at 450° C. for twelve hours. It is then ready for use in the reactor. Other precursors, such as cerium nitrate, can also be used to produce the desired catalyst. Other techniques, such as spray or tumble-drying, known to those skilled in the art, also can be used to apply the catalyst.

A variety of catalysts are commonly applied to catalyst supports for use in the production of organic compounds and specifically in the production of ketones such as MCPK. These catalysts include, but are not limited to, metal or metal oxides such as the oxides of cerium ($CeO_2$ or $CeO_3$), zirconium ($ZrO_2$), zinc (ZnO), or other lanthanides, group IIIB, IVB and VB metals or metal oxides. Conventionally, standard weight percentages of catalyst per unit weight of the support are prepared. For example, a 5% catalyst comprises 0.05 grams of catalyst per gram of catalyst support. Catalysts of 5%, 10% and other multiples of 5% are commonly prepared. This is accomplished by techniques known to those skilled in the art.

In a preferred embodiment, a solution of the catalyst or a precursor to the catalyst is applied to an effective surface area of a support material such that there is substantially a theoretical monolayer of desired catalyst present. Further heat treatment of a catalyst precursor forms the catalyst. It has been found that a theoretical monolayer of catalyst optimizes the catalysis conditions. Specifically, an optimal quantity of catalyst is available to facilitate the desired reaction. Thus, the negative effects of the exposed catalyst support are eliminated in the case where there is too little catalyst and the negative effects of filling pores and losing effective surface area are eliminated in the case where there is too much catalyst. Accordingly, the catalyst structure in accordance with the present invention includes a catalyst support with an effective surface area and a substantially theoretical monolayer of catalyst applied to such effective surface area. As used herein, a substantially theoretical monolayer shall mean plus or minus 10% of a theoretical monolayer. "Theoretical monolayer" refers to a film or layer of a material (catalyst) on a surface at a thickness of one molecule.

The catalyst is expressed as weight percent of catalyst per unit weight of catalyst support. By applying a theoretical monolayer of catalyst to the effective surface area of a catalyst support, catalysis conditions are optimized. Although conventional catalyst supports useful for the production of organic compounds generally and ketones specifically having effective surface areas ranging from about 20 to 500 $m^2$ per gram of support, the preferred catalyst support material for use in the production of ketones in accordance with the present invention has an effective surface area of about 20 to 500 $m^2$ per gram of support, more preferably about 20 to 200 $m^2$ per gram and most preferably about 30 to 180 $m^2$ per gram of support.

By providing a substantially theoretical monolayer of catalyst to the catalyst support to optimize the catalyst structure, it has been found that the weight hour space velocity (WHSV) of the reaction can be significantly increased without significantly adversely affecting the conversion or selectivity of the desired reaction. Specifically, a substantial theoretical monolayer catalyst in accordance with the present invention facilitates a WHSV of greater than 1, more preferably greater than 5, and most preferably greater than 10.

A first step in making the catalyst structure of the present invention is to determine the amount of catalyst needed to provide a theoretical monolayer of that catalyst to a particular catalyst support. By knowing the effective surface area of a catalyst support and by knowing the crystallographic data for the catalyst, the theoretical monolayer for that catalyst can be calculated.

The effective surface area of commercially available catalyst supports is commonly provided by the supplier of the support material or can be measured using various commercially available instruments. There are numerous types of commercial instruments used to determine surface areas by adsorption of liquid nitrogen (the "BET" method). One of these instruments calculates the surface area based on a full adsorption/desorption Volume of $N_2$ vs. Pressure curve at a range of pressures between roughly $10^{-3}$ torr and 760 torr (0.133 KPa to $102(10^3)$ KPa). This method gives very accurate numbers, but is time consuming. Newer instruments are fully automated and have liquid nitrogen flow controllers. Another instrument estimates the surface area from the BET equation and adsorption/desorption at only a single pressure and is a much quicker method. The surface areas obtained seldom differ from more accurate numbers by more than 10%. Effective surface area of a catalyst support is commonly expressed in the form of surface area or square units per weight of the catalyst support. Typical effective surface area information is expressed in square meters per gram or $m^2/g$.

The ketones produced by the method and apparatus of this invention are useful in the preparation of agricultural and herbicidal compounds.

The above description and accompanying drawing are provided for the purpose of describing embodiments of the invention and are not intended to limit the scope of the invention in any way. It will be apparent to those skilled in the art that various modifications and variations can be made in the process for the production of a ketone without departing from the spirit or scope of the invention. Thus, it is intended that the present invention cover the modifications and variations of this invention provided they come within the scope of the appended claims and their equivalents.

What is claimed is:

1. A method for the production of a ketone comprising:
   providing a tube reactor having a catalytic bed;
   providing a raw material feed comprising a carboxylic acid, a source of oxygen, and an aldehyde; and
   passing the raw material feed comprising the carboxylic acid, the source of oxygen, and the aldehyde, each in a vapor phase, through the catalytic bed at a weight hourly space velocity greater than one to form the ketone.

2. The method of claim 1, wherein the ketone is an asymmetrical ketone.

3. The method of claim 1, wherein the carboxylic acid and the aldehyde are heated before entering the tube reactor.

4. The method of claim 1, wherein the weight hourly space velocity is in the range of 1 to 20.

5. The method of claim 1, wherein the weight hourly space velocity is in the range of 2 to 20.

6. The method of claim 1, wherein the reacting takes place in two or more tube reactors connected in parallel.

7. The method of claim 1, wherein, in the reacting step, the catalyst is a theoretical monolayer on a solid support.

8. The method of claim 1, further comprising the step of recovering the ketone.

9. The method of claim 1, wherein the source of oxygen is water.

10. The method of claim 1, wherein the ketone is methyl cyclopropyl ketone.

11. The method of claim 1, wherein the aldehyde is cyclopropanecarboxaldehyde.

12. The method of claim 1, wherein the acid is acetic acid.

13. The method of claim 1, wherein the weight ratio of the carboxylic acid: source of oxygen: aldehyde ranges from 1:1:1 to 20:1:1.

14. The method of claim 1, wherein the catalyst is selected from MgO, $TiO_2$, $ZrO_2$, ZnO, $CeO_2$, and $Ce_2O_3$.

15. The method of claim 14, wherein the catalyst is $CeO_2$ on a $TiO_2$ support.

16. The method of claim 15, wherein there is about 15 to 20% $CeO_2$ per gram of $TiO_2$.

17. The method of claim 1, wherein the method is a continuous process.

18. A method of preparing a ketone comprising:
   providing a plurality of tube reactors, each having a catalytic bed;
   providing a raw material feed comprising a carboxylic acid, a source of oxygen, and an aldehyde, to produce the ketone;
   selectively passing the raw material feed through the catalytic bed of at least one of the plurality of tube reactors at a temperature of between about 350° C. and 500° C. and a weight hourly space velocity of greater than 1; and
   recovering the ketone.

19. The method of claim 18, comprising selectively stopping the passage of raw material feed through the catalytic bed of the at least one tube reactor and passing the raw material feed through the catalytic bed of at least one of the plurality of tube reactors.

20. The method of claim 19, comprising regenerating the catalytic bed of the at least one tube reactor through which the passage of raw material feed has been stopped.

21. The method of claim 18, wherein the catalytic bed includes a $CeO_2/TiO_2$ catalyst structure having about 15 to 20% $CeO_2$ per gram of $TiO_2$.

22. A process for the production of a ketone comprising:
   reacting acetic acid with cyclopropanecarboxaldehyde and with water to form methyl cyclopropyl ketone;
   wherein the reacting occurs in the vapor phase and in the presence of a catalyst.

* * * * *